United States Patent [19]

Borer et al.

[11] Patent Number: 4,648,713
[45] Date of Patent: Mar. 10, 1987

[54] METHOD AND CUVETTE FOR PHOTOMETRIC ANALYSIS

[75] Inventors: Claude Borer; Kurt Schildknecht, both of Hünenberg, Switzerland

[73] Assignee: Hoffmann-La Roche Inc., Nutley, N.J.

[21] Appl. No.: 565,246

[22] Filed: Dec. 23, 1983

[30] Foreign Application Priority Data

Dec. 29, 1982 [CH] Switzerland ................ 7611/82

[51] Int. Cl.⁴ .............................. G01N 1/10
[52] U.S. Cl. .................. 356/246; 356/428; 356/436; 356/440
[58] Field of Search ............. 356/246, 436, 440, 428

[56] References Cited

U.S. PATENT DOCUMENTS

| | | | |
|---|---|---|---|
| 2,761,067 | 8/1956 | Troy | 250/43.5 |
| 3,506,367 | 4/1970 | Ross et al. | 356/246 |
| 3,526,462 | 9/1970 | McCurdy et al. | 356/246 |
| 3,627,432 | 12/1971 | Bergmann | 356/246 |
| 3,843,269 | 10/1974 | Hohberg et al. | 356/205 |
| 4,099,882 | 7/1978 | Andren et al. | 356/181 |
| 4,357,301 | 11/1982 | Cassady et al. | 422/64 |

FOREIGN PATENT DOCUMENTS

| | | |
|---|---|---|
| 497567 | 6/1978 | Australia . |
| 2049522 | 4/1971 | Fed. Rep. of Germany . |
| 2160836 | 6/1973 | Fed. Rep. of Germany . |
| 2810177 | 9/1979 | Fed. Rep. of Germany . |
| 804984 | 11/1936 | France . |

*Primary Examiner*—John E. Kittle
*Attorney, Agent, or Firm*—Jon S. Saxe; Bernard S. Leon; Mark E. Waddell

[57] ABSTRACT

A method for the photometric analysis of a liquid sample in which different path lengths of the sample are analyzed photometrically.

In order to reduce the time needed for analyzing a large number of samples, the analysis is carried out with a light beam which is generated by an immobile light source; the sample is introduced into a cuvette which has at least two regions with different cross-section lengths; and the cuvette is continuously moved along a circular path in such a manner that in the course of the photometric measurement the light beam passes through at least two of the regions in succession.

10 Claims, 4 Drawing Figures

METHOD AND CUVETTE FOR PHOTOMETRIC ANALYSIS

FIELD OF THE INVENTION

The invention is concerned with a method for the photometric analysis of a liquid sample in which different path lengths of the sample are measured photometrically, and with a cuvette suitable for carrying out such a method.

BACKGROUND OF THE INVENTION

In the photometric measurement of the light absorption of a liquid sample which is contained in a cuvette, the light beam exiting from the cuvette is measured by means of a photocell. Within a given range of light intensity, the voltage given off by the cell is approximately a linear function of the intensity of the light incident upon the photocell. However, the range of light intensity over which the cell exhibits such a linear response is limited and is very much smaller than the range over which light absorption can vary. This is allowed for by carrying out the measurements at different path lengths, a longer path length being chosen if the absorbance of the sample is small and a shorter path length being chosen if the absorbance of the sample is large. It is known (German Offenlegungsschrift No. 28 10 117) to carry out such measurements by using in a vertical position an elongated cuvette which has, distributed along its length, regions with different cross-section lengths and different thicknesses of the cuvette wall, the cross-section length and the wall thickness changing stepwise. In this known method, the cuvette is raised or lowered to move the region of whichever path length is desired into the path of the rays between the light source and the photocell.

Since in the known method it is necessary to raise or lower individual cuvettes in order to change the measured path length, the method is not suitable for the rapid analyses of samples in a large number of cuvettes. Moreover, the form of the cuvette used in the known method makes necessary a relatively large volume of sample. Since the thickness of the cuvette wall and hence the resulting light absorption differs in the various regions of the known cuvette, this difference must be taken into consideration when determining the result of a measurement, which naturally constitutes an additional complication.

It is the main object of the present invention to provide a method of the type mentioned hereinbefore which is not accompanied by the aforementioned limitation in use and the aforementioned disadvantages and which thus makes possible, in particular, rapid analyses of samples in a large number of cuvettes, with small amounts of sample, and that in as simple a manner as possible. It is a further object of the invention to provide a cuvette which is suitable for carrying out such a method.

SUMMARY OF THE INVENTION

This object is achieved according to the invention by means of a method in which the analysis is carried out with a light beam which is generated by an immobile light source; the sample is introduced into a cuvette which has at least two regions with different cross-section lengths; and the cuvette is continuously moved along a circular path in such a manner that in the course of the photometric measurement the light beam passes through at least two of the regions in succession.

The advantages provided by the invention are essentially that it makes possible, with relatively little effort, rapid analyses of samples in a large number of cuvettes.

In a preferred embodiment of the method provided by the invention, the light beam runs in a horizontal plane and the longitudinal axis of each cuvette is at a right angle to this plane.

In a second embodiment of the method provided by the invention, during the movement of the cuvette its longitudinal axis is in a horizontal plane and the light beam runs at a right angle to this plane.

In a third embodiment of the method provided by the invention, during the movement of the cuvette its longitudinal axis is in a horizontal plane, the light beam runs in this plane or in a plane parallel thereto, and the regions of the cuvette which have been provided for the photometric measurement extend between the surface of the sample in the cuvette and a step-shaped bottom of the cuvette. This embodiment has the advantage that it permits measurements with variable path length in each portion, i.e. with a path length which is not exclusively determined by the dimensions of the cuvette but also by the amount of sample.

The invention is also concerned with a cuvette suitable for carrying out the method provided by the invention, said cuvette having an elongated interior which has at one end and distributed over its width at least two adjacent regions which are suitable for carrying out the photometric measurement and which have different cross-section lengths, the cross-section length changing from one region to the next in a stepwise manner. Since the aforementioned regions lie side by side at one end of the cuvette, the cuvette enables measurements to be carried out with a relatively small amount of sample.

In a preferred embodiment of this cuvette, each region extends between two flat walls of the cuvette which are optically transparent and which are parallel to each other, the distance between the inside faces of these walls defining the analysed path length of the sample and all regions extending between walls which have the same thickness. This embodiment has the advantage that during the photometric measurement the light absorption by the cuvette walls is the same in all regions of the cuvette. This arrangement simplifies the determination of the measured results.

BRIEF DESCRIPTION OF THE DRAWINGS

A detailed description of the preferred embodiments will now be given, having reference to the drawings in which.

DETAILED DESCRIPTION OF THE PREFERRED EMBODIMENTS

Example 1

Figure 1:
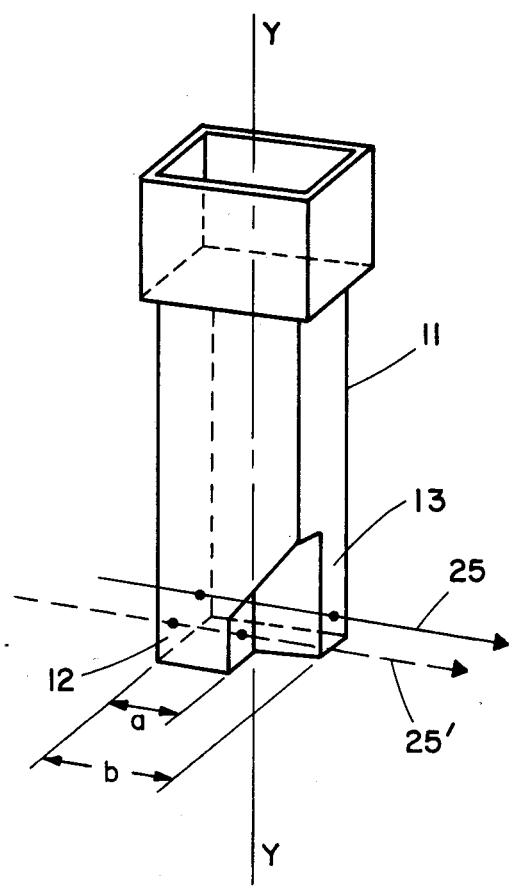
FIG. 1 shows a diagrammatic perspective view of a cuvette provided by the invention.

FIG. 1 shows a cuvette 11 which is suitable for carrying out the method provided by the invention. This cuvette has an elongated interior and a longitudinal axis Y—Y. The interior of the cuvette has at one end, distributed over its width, two adjacent regions 12 and 13 which are suitable for carrying out the photometric measurement of a liquid sample contained in the cuvette and which have different cross-section lengths. According to the invention, the cuvette can also have more than two such regions. Each of the regions 12, 13 extends between two flat walls of the cuvette which are optically transparent and parallel to each other, the respective distances (a) and (b) between the inside faces of these walls defining the analysed path length of the sample which is analysed in the region. This distance changes from one region to the next in stepwise fashion. Adjacent regions thus enable different path lengths of the sample to be analyzed. All regions extend between walls which have the same thickness.

Figure 2:
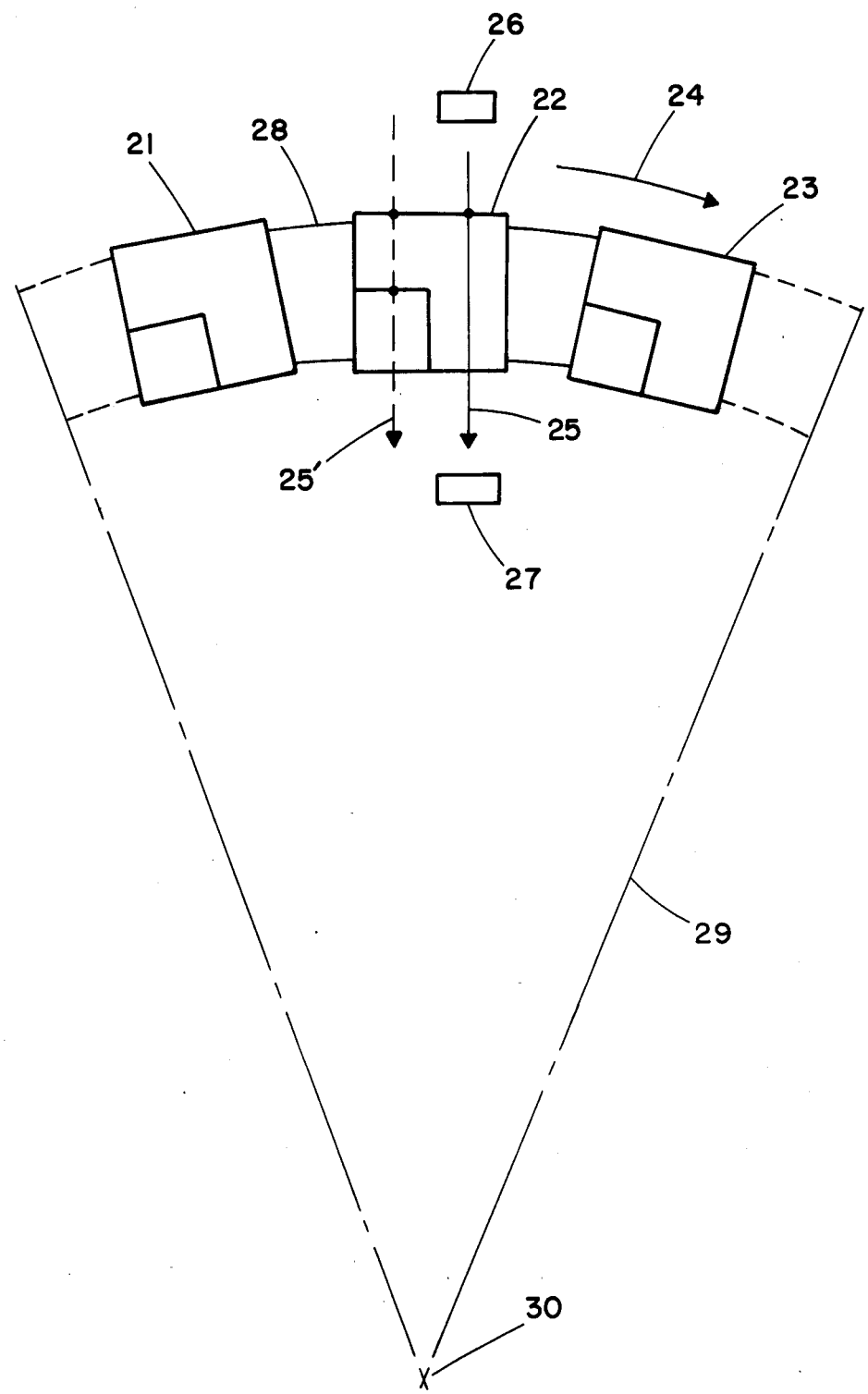
FIG. 2 shows a diagrammatic plan view of a measuring arrangement with a circular arrangement of cuvettes of the type shown in FIG. 1.

The cuvette described above can be used singly or in groups. As shown in FIG. 2 by a diagrammatic plan view, it is advantageous in the latter case to provide connecting pieces 28 which connect adjacent cuvettes by being, for example, welded to the cuvettes. In this manner, self-supporting groups of cuvettes can be formed. By suitably constructing the connecting pieces there can be formed groups of cuvettes which can together form, for example, a circular arrangement of cuvettes. FIG. 2 shows a diagrammatic plan view of such a cuvette group.

The cuvettes and the connecting pieces are preferably made of glass-clear unstabilized polymethyl methacrylate (PMMA).

The method provided by the invention is carried out by introducing the liquid sample into one of the cuvettes described above. These cuvettes are arranged singly or, as shown in FIG. 2, as part of a group of cuvettes on a cuvette support 29 which is, for example, a circular disc which has a circular arrangement of openings (not shown in FIG. 2) into which the cuvettes are inserted. The cuvettes are held in these openings, for example, by an upper cuvette rim (not shown in the drawings).

As shown in FIG. 2, the photometric measurement is carried out using a light beam 25 which is generated by an immobile light source 26. The light beam exiting from a cuvette is received by a light receiver 27 which generates a corresponding electrical signal. The light beam runs in a horizontal plane and the longitudinal axis of each cuvette is directed at a right angle to this plane.

As can be seen from FIG. 1, the path of the rays is preferably at approximately half the height of regions 12 and 13 of each cuvette 11.

By rotating the cuvette support 29 about its axis 30 in the direction indicated by arrow 24, each cuvette such as, for example, cuvette 21 in FIG. 2 is moved continuously along a circle in a plane which is at a right angle to the longitudinal axis Y—Y of the cuvette. As a result, the light beam 25 passes rapidly and in succession through all the regions of the cuvette and, in so doing, passes through the different path lengths of the sample. In FIGS. 1 and 2 the broken line and arrow 25' mark the part of the region 12 through which the light beam 25 passes when this part is between the light source 26 and the light receiver 27.

Example 2

Figure 3:
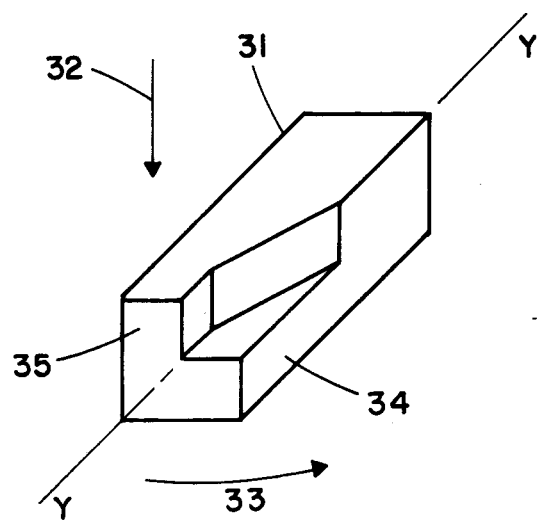
FIG. 3 shows a diagrammatic perspective view of a variant of the measuring arrangement shown in FIG. 2.

A variant of the method described in Example 1 will now be described with reference to FIG. 3. In this variant there is provided a cuvette 31 having similar regions 34, 35 as the cuvette 11 in FIG. 1 and which additionally contains one or more chambers (not shown in FIG. 3) containing the liquid sample or its components as long as the cuvette is int the stationary state, and, on centrifuging the cuvette support, the sample or its components pass into the cuvette regions 34, 35 which are provided for performing the photometric measurements.

During the movement of the cuvette 31 by centrifuging the cuvette support, the longitudinal axis Y—Y of the cuvette is in a horizontal plane. A light beam 32 which is provided for the photometric measurement through the regions 34, 35 passes at a right-angle to this plane. The cuvette is moved in the direcuon shown by the arrow 33.

It is a prerequisite for carrying out a correct measurement by means of this variant of the method that the cuvette support is centrifuged with a sufficiently high speed of rotation so that the resulting centrifugal force holds the liquid sample in the regions 34, 35 of the cuvette. It is of course a further prerequisite that the regions 34, 35 contain a sufficient amount of the sample, so that the light beam 32 passes through the sample in both regions.

Example 3

Figure 4:
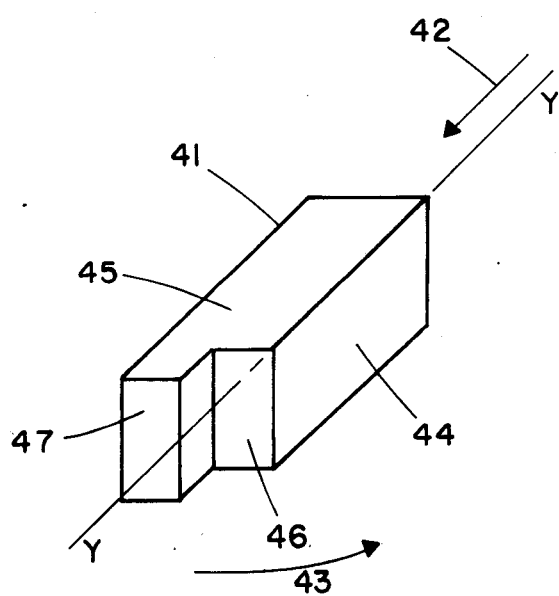
FIG. 4 shows a diagrammatic perspective view of a variant of the measuring arrangement shown in FIG. 3.

A variant of the method described in Example 2 is carried out with a cuvette 41 which has a different shape. As shown in FIG. 4, at one end of the cuvette there are provided for a photometric measurement regions 44, 45 which, distributed over the length of the cuvette, have different cross-section lengths, the cross-section length changing from one region to the next in a stepwise manner. The cuvette can have more than two such regions.

During the movement of the cuvette 41 by centrifuging the cuvette support, the longitudinal axis of the cuvette is, as in Example 2, in a horizontal plane. A light beam 42 which is provided for the photometric measurement through the regions 44, 45 runs in this plane or in a plane parallel thereto.

In this Example, each region 44 and 45 extends between the inside face of a cuvette wall 46 and 47 respectively, and the free surface of the liquid sample contained in the cuvette. This variant thus enables measurements to be carried out at variable path lengths according to the choice of sample volume.

We claim:

1. A method for the photometric analysis of liquid samples in which different thicknesses of each sample are analyzed photometrically comprising the steps of:
    (a) introducing the sample to be analyzed into a cuvette, which is provided with at least two regions defined by the shape of the cuvette, which regions have different cross-sectional lengths for receiving the sample;
    (b) continuously moving the cuvette along a circular path;
    (c) passing a light beam generated by an immobile light source along a path which crosses said circular path, whereby during the cuvette's circular movement, the light beam passes through the sample contained in said at least two regions in succession and;
(d) analyzing the sample photometrically, so that the analysis of the sample is effected on those portions of the sample which have different thicknesses by reason of being received in said at least two regions.

2. A method according to claim 1, wherein the path of the light beam lies in a horizontal plane and wherein the longitudinal axis of the cuvette is at a right angle to this plane.

3. A method according to claim 1, wherein during the movement of the cuvette, its longitudinal axis is in a horizontal plane and the light beam is directed at a right angle to this plane.

4. A method according to claim 1, wherein during the movement of the cuvette, the longitudinal axis is in a horizontal plane, the path of the light beam lies in this plane or in a plane parallel thereto, and the said at least two regions of the cuvette which are provided for the photometric measurement extend between the surface of the sample in the cuvette facing the open end of the cuvette and a step-shaped bottom of the cuvette.

5. A cuvette for the photometric analysis of a liquid sample in an automatic photometric analyzer wherein the cuvette is moved across a light beam while traveling in a circular path, comprising an elongated interior for retaining the liquid sample and which elongated interior defines at least two adjacent regions distributed over its width, which are suitable for carrying out the photometric analysis, each such region defining a sight passageway, and which sight passageways have different lengths changing from one region to the next in a stepwise manner, whereby as the cuvette is being moved through the light beam, the light beam passes through the respective sight passageways of said at least two adjacent regions in succession.

6. A cuvette according to claim 5, wherein each region extends between two flat walls of the cuvette which are optically transparent and which are parallel to each other, the distance between the inside faces of these walls defining the cross-sectional length along the sight passageway, and wherein all regions are defined by walls of the cuvette which have the same thickness.

7. A self supporting group of cuvettes for the photometric analysis of a plurality of liquid samples in an automatic photometric analyzer wherein the cuvettes are moved across a light beam while traveling in a circular path, comprising two or more cuvettes each cuvette having an elongated interior for retaining the liquid sample and which elongated interior defines at least two adjacent regions distributed over its width, which are suitable for carrying out the photometric analysis, each such region defining a sight passageway, and which sight passageways have different lengths changing from one region to the next in a stepwise manner, whereby as the cuvette is being moved through the light beam, the light beam passes through the respective sight passageways of said at least two adjacent regions in succession, said self supporting group further comprising means for supporting said cuvettes for movement in a circular path.

8. A self supporting group of cuvettes according to claim 7, wherein in each cuvette, each said region extends between two flat walls of the cuvette which are optically transparent and which are parallel to each other, the distance between the inside faces of these walls defining the length of the sight passageway, and wherein all regions are defined by walls of the cuvette which have the same thickness.

9. The self supporting group of cuvettes according to claim 7, wherein the cuvettes are arranged in a circle.

10. The self supporting group of cuvettes according to claim 8, wherein the cuvettes are arranged in a circle.

* * * * *